United States Patent [19]

Lind et al.

[11] 4,079,063

[45] Mar. 14, 1978

[54] PROCESS FOR THE PREPARATION OF 2-PHENYL-4-HYDROXY-1,2,3-TRIAZOLE-1-OXIDES

[75] Inventors: Hanns Lind, Liestal; Haukur Kristinsson, Bottmingen, both of Switzerland

[73] Assignee: Ciba-Geigy Corporation, Ardsley, N.Y.

[21] Appl. No.: 663,331

[22] Filed: Mar. 3, 1976

Related U.S. Application Data

[63] Continuation of Ser. No. 501,392, Aug. 28, 1974, abandoned.

[30] Foreign Application Priority Data

Sep. 10, 1973 Switzerland .................. 12960/73

[51] Int. Cl.$^2$ .................................. C07D 249/06
[52] U.S. Cl. ........................... 260/308 A; 260/193; 260/566 A; 424/200
[58] Field of Search .................... 260/308 A

[56] References Cited

U.S. PATENT DOCUMENTS

| 2,705,713 | 4/1955 | Kendall et al. ........... 260/308 A |
| 3,666,758 | 5/1972 | Dorlars et al. ........... 260/308 A |

FOREIGN PATENT DOCUMENTS

| 1,168,437 | 4/1964 | Germany .................. 260/308 A |

OTHER PUBLICATIONS

Jagerspacher, Ber. Dent. Chem., vol. 28, pp. 1283–1287, (1895).
Benson, Chemical Reviews, vol. 46, pp. 20, 36–38, 52 (1950).
Elderfield, Heterocyclic Compounds, vol. 7, (New York, 1961), p. 413.

*Primary Examiner*—Alton D. Rollins
*Attorney, Agent, or Firm*—Harry Falber

[57] ABSTRACT

Process for the preparation of 2-phenyl-4-hydroxy-1,2,3-triazole-1-oxides of the formula

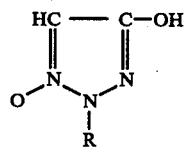

from oxime-hydrazones of the formula

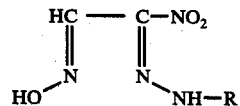

in which formulae R stands for an unsubstituted or substituted phenyl group.

4 Claims, No Drawings

PROCESS FOR THE PREPARATION OF 2-PHENYL-4-HYDROXY-1,2,3-TRIAZOLE-1-OXIDES

This is a continuation of application Ser. No. 501,392 filed on Aug. 28, 1974, now abandoned.

The present invention relates to a process for the preparation of 2-phenyl-4-hydroxy-1,2,3-triazole-1-oxides.

It is known from the German Pat. No. 1,168,437 that azo compounds of the formula

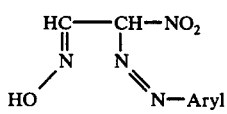

obtainable by reaction of diazotised arylamine with methazonic acid, which may be interpreted also as being oxime hydrazones of the formula

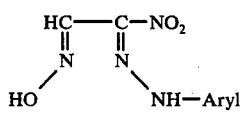

can be cyclized in aqueous-alkaline medium in the presence of acid anhydrides or acid halides at a temperature of between 0° and +50° C to give 2-aryl-4-nitro-1,2,3-triazoles.

It has now been found that, surprisingly, 2-phenyl-4-hydroxy-1,2,3-triazole-1-oxides of formula I

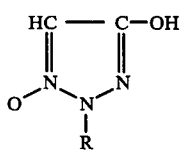

wherein R represents a substituted or unsubstituted phenyl radical
can be obtained in a simple manner by the reaction of an oxime hydrazone of formula II

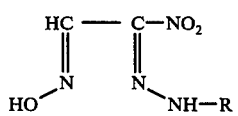

wherein R has the meaning given under formula I, in the presence of a lower aliphatic carboxylic acid at a temperature of between 15° and 100° C.

Suitable lower aliphatic carboxylic acids are those having 1 to 5 carbon atoms, e.g., formic acid, propionic acid, butyric acid and, preferably, acetic acid. Mixtures of these acids with water are advantageously used, the water content of the mixtures being 1 to 25%, preferably 5 to 10%. The reaction is preferably performed at a temperature of between 20° and 30° C. The duration of the reaction is from 1 to 24 hours.

Substituents on the phenyl radical R are, for example, one or more identical or different fluorine, chlorine, bromine and/or iodine atoms, alkyl, haloalkyl, cyano, alkoxy, nitro, alkoxycarbonyl, alkylthio, alkylsulphonyl, alkylsulphinyl, acetylamino, amino, monoalkylamino, dialkylamino, phenoxy and/or phenylsulphonyl groups. The alkyl groups present as substituents, or in the substituents, on the phenyl radical can have 1 to 5 carbon atoms.

The oxime hydrazones of formula II used as starting compounds are obtainable in a simple manner by coupling of a diazotised aromatic amine, derived from the radical R, with methazonic acid. For this purpose, the solution of the diazonium salt, prepared in the normal manner, is added at 0° to 10° C to an acetic acid/aqueous methazonic acid solution containing sodium acetate. Methazonic acid itself can be obtained, for example, by the method described in 'Journal fur praktische Chemie' [2], Vol. 81, p. 203 [1910].

The 2-phenyl-4-hydroxy-1,2,3-triazole-1-oxides obtainable according to the invention can be reduced in a simple manner, in the presence of glacial acetic acid, by means of zinc dust to the corresponding 2-phenyl-4-hydroxy-1,2,3-triazoles. This reduction can be performed advantageously immediately after ring closure in the reaction mixture.

The 2-phenyl-4-hydroxy-1,2,3-triazole-1-oxides of formula I producible according to the invention and the 2-phenyl-4-hydroxy-1,2,3-triazoles obtainable from these by reduction can additionally be chlorinated or brominated in the 5-position. This chlorination or bromination can be carried out with elementary chlorine or bromine, or by the action of N-chlorosuccinimide or N-bromosuccinimide, in solvents inert to these agents, such as in halogenated hydrocarbons, preferably carbon tetrachloride.

The 2-phenyl-4-hydroxy-1,2,3-triazole-1-oxides obtainable according to the invention, as well as the subsequent products, prepared from these by reduction and/or by halogenation, of formula Ia

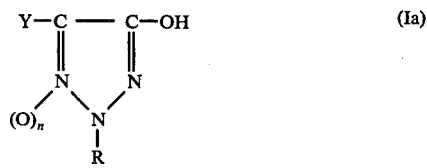

wherein Y represents hydrogen, chlorine or bromine, and $n$ denotes 0 or 1, and R has the meaning given under formula I, have an insecticidal, fungicidal, bactericidal and nematicidal action. Furthermore, these compounds are valuable starting materials for the preparation of phosphoric acid esters having an insecticidal action. Such phosphoric acid esters are described, for example, as corresponding to the formula

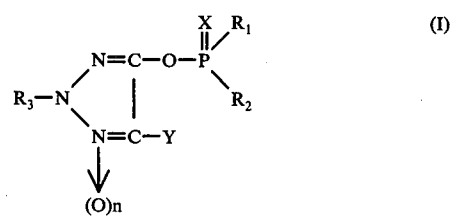

wherein
$R_1$ represents alkyl, alkoxy, alkylthio, alkoxyalkylthio, amino, monoalkylamino, dialkylamino or unsubstituted or substituted phenyl,
$R_2$ represents alkoxy, alkylthio, amino, monoalkylamino or dialkylamino,
$R_3$ represents unsubstituted or substituted phenyl, Y represents hydrogen, chlorine or bromine,
n represents the numbers 0 or 1, and
X represents oxygen or sulphur.

Substituents of the phenyl groups in the case of $R_1$ and $R_3$ are, for example, one or more identical or different fluorine, chlorine, bromine and/or iodine atoms, alkyl, haloalkyl, cyano, alkoxy, nitro, alkoxycarbonyl, alkylthio, alkylsulphonyl, alkylsulphinyl, acetylamino, amino, monoalkylamino, dialkylamino, phenoxy and/or phenylsulphonyl groups.

The compounds of formula I can be prepared by the following methods known per se:

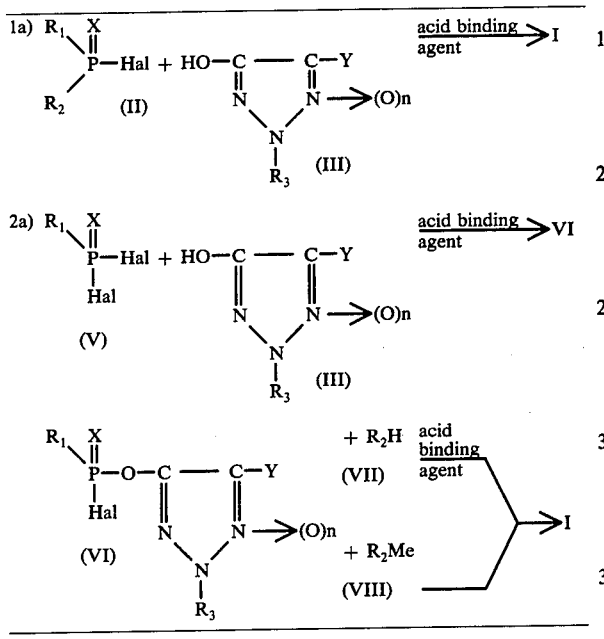

In formulae II, III and V to VIII, the symbols $R_1$ to $R_3$, X, Y and $n$ have the meaning given for formula I, Hal stands for fluorine, chlorine, bromine or iodine, particularly, however, for fluorine, chlorine or bromine, $R'_2$ stands for alkoxy or alkylthio, and Me denotes a monovalent metal, preferably an alkali metal, especially sodium or potassium. Suitable acid-binding agents are, for example, the following bases: tertiary amines such as triethylamine, dimethylaniline, pyridine, inorganic bases such as hydroxides and carbonates of alkali metals and alkaline-earth metals, preferably sodium and potassium carbonate. The reactions 1a and 2a are performed under normal pressure, at a temperature of 0° – 150° C, and preferably in solvents or diluents which are inert to the reactants. Suitable solvents or diluents are, for example: aromatic hydrocarbons such as benzene, toluene, ligroins; halogenated hydrocarbons such as chlorobenzene, polychlorobenzenes, bromobenzene; chlorinated alkanes having 1 to 3 carbon atoms; ethers such as dioxane, tetrahydrofuran; esters such as acetic acid ethyl ester; ketones such as methyl ethyl ketone, diethyl ketone; nitriles, etc.

The compounds of formula I have a broad biocidal action, and can be used for the control of various animal and plant pests.

They are particularly suitable for the control of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae.

The insecticidal action can be appreciably broadened and adapted to suit given circumstances by the addition of other insecticides.

The compounds of formula I can be used on their own or together with suitable carriers and/or additives. Suitable carriers and additives may be solid or liquid, and they correspond to the substance common in formulation practice, such as, for example, natural or regenerated substances, solvents, dispersing agents, wetting agents, adhesives, thickeners, binders and/or fertilizers.

For application, the compounds of formula I can be processed into the form of dusts, emulsion concentrates, granulates, dispersions, sprays or solutions, the formulation of these preparations being effected in a manner commonly known in practice. Cattle dips and spray races in which aqueous preparations are used, should also be mentioned.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparations: — dusts, scattering agents, granulates, coated granulates, impregnated granulates and homogeneous granulates;

liquid preparations:
 (a) water-dispersible active-substance concentrates: wettable powders, pastes, emulsions;
 (b) solutions.

The content of active substance in the above-described agents is between 0.1 and 95%; it is to be mentioned in this connection that in the case of application of the agents from an aeroplane, or by means of some other suitable application devices, concentrations of up to 99.5% can be used, or even the pure active substance.

As is clear from the foregoing, the process of the invention provides also, by way of the directly obtainable 2-phenyl-4-hydroxy-1,2,3-triazole-1-oxides of formula I, an easy access to the corresponding 2-phenyl-4-hydroxy-1,2,3-triazoles. From this class of substances, the only compound hitherto known is the 2-phenyl-4-hydroxy-1,2,3-triazole unsubstituted in the phenyl radical. It is prepared by firstly converting glyoxal by reaction with phenylhydrazine into glyoxal-diphenylhydrazone, and then condensing this in the presence of copper sulphate to 2-phenyl-1,2,3-triazole (cp. J. L. Riebsomer, J. Org. Chem. 13, (1948), 815). This is subsequently converted with fluorosulphone methyl ester into 2-phenyl-3-methyl-1,2,3-triazolium fluorosulphonate, which yields, after treatment with N-bromosuccinimide and sodium hydroxide solution, 2-phenyl-3-methyl-1,2,3-triazolin-4-one (see M. Begtrup et al., Acta Chem. Scand. 25, (1971), 2087). The last-mentioned compound is then converted by reaction with benzoyl chloride into 2-phenyl-4-benzoyloxy-1,2,3-triazole, which yields, on alkaline hydrolysis, 2-phenyl-4-hydroxy-1,2,3-triazole (see M. Gegtrup, Acta Chem. Scand. 26, 1972 715).

Although in principle it should be possible to also obtain by the above process the 2-phenyl-4-hydroxy- 1,2,3-triazoles substituted in the phenyl radical, and from these the corresponding 1-oxides, this process in practice is scarcely to be contemplated since on the one hand it is very involved, and on the other hand it gives the desired final products in a yield only of less than 10% of theory, relative to the starting materials, glyoxal and phenylhydrazine. The present invention thus provides, for the first time, a process rendering possible the preparation of 2-phenyl-4-hydroxy-1,2,3-triazole-1-oxides and the corresponding 2-phenyl-4-hydroxy-1,2,3-triazoles in a simple and economic manner.

The present invention is further illustrated by the following examples.

EXAMPLE 1

2-Phenyl-4-hydroxy-1,2,3-triazole-1-oxide (corresponding to formula I)

A diazonium salt solution of 2 moles of aniline, prepared in the usual manner, is added at 0° to 10° C, with stirring, to an acetic acid/aqueous methazonic acid solution containing sodium acetate, produced from 244 g of nitromethane (4 moles).

The yellow oxime-hydrazone of formula II (R = phenyl) precipitates out as a thick suspension.

The precipitate, still moist, (water content about 60%) is stirred at room temperature into 3000 ml of glacial acetic acid. There is formed after a short time, with the escape of nitrous gases, a clear dark solution, which is stirred overnight and subsequently concentrated by evaporation to dryness. The solid residue is washed with ether, filtered off under suction and dried. After recrystallization from acetonitrile, the yield of final product is 210 g = 59% relative to the nitromethane; M.P. 155°–156° C (decomposition).

| Analysis: | C | H | N | O |
|---|---|---|---|---|
| calculated: | 54.3 | 3.95 | 23.7 | 18.1 |
| found: | 54.0 | 3.9 | 23.3 | 18.5. |

EXAMPLE 2

2-(3,4-dichlorophenyl)-4-hydroxy-1,2,3-triazole-1-oxide (corresponding to formula I)

The oxime-hydrazone, still moist, (corresponding to formula II; R = 3,4-dichlorophenyl), prepared in a known manner from 1 mole of diazotised 3,4-dichloroaniline and methazonic acid, analogously to Example 1, is stirred at room temperature into 2000 ml of glacial acetic acid. There is formed after a few hours, with the formation of nitrous gases, a clear dark solution, and a short time later the product begins to precipitate; it is filtered off after 24 hours and dried.

Yield: 172 g (70% of theory, relative to nitromethane);
M.P. 183°–184° C (decomposition).

| Analysis: | C | H | Cl | N | O |
|---|---|---|---|---|---|
| calculated: | 39.0 | 2.0 | 28.9 | 17.1 | 13.0 |
| found: | 39.3 | 2.0 | 29.3 | 16.6 | 12.8. |

EXAMPLE 3

2-(2-Chlorophenyl)-4-hydroxy-1,2,3-triazole-1-oxide 100 g of oxime-hydrazone II (R = 2-chlorophenyl), prepared from diazotized 2-chloroaniline and methazonic acid, is stirred in 1000 ml of 90% acetic acid at room temperature. There are formed after a short time nitrous gases, and a dark clear solution is obtained. After 10 hours, the solution is concentrated by evaporation to dryness, and the residue is stirred into ether, filtered off under suction and dried.

Yield: 45 g = 52% of theory.
M.P. 161°–163° C (decomposition).

| Analysis: | C | H | Cl | N |
|---|---|---|---|---|
| calculated: | 45.4 | 2.8 | 16.8 | 19.85 |
| found: | 44.8 | 2.9 | 16.4 | 19.3. |

EXAMPLE 4

2-(4-Carbethoxyphenyl)-4-hydroxy-1,2,3-triazole-1-oxide 280 g of oxime-hydrazone II (R = carbethoxyphenyl), prepared from diazotised 4-aminobenzoic acid-ethyl ester and methazonic acid, is stirred in 2000 ml of acetic acid for 10 hours at 60° C. The whole is cooled and the precipitate is filtered off with suction, well washed with water and again filtered off with suction.

Yield: 130 g = 52% of theory.
M.P.: 186° C.

| Analysis: | C | H | N |
|---|---|---|---|
| calculated: | 53.0 | 4.4 | 16.9 |
| found: | 53.0 | 4.3 | 16.65. |

EXAMPLE 5

2-Phenyl-4-hydroxy-1,2,3-triazole 88.5 g of 2-phenyl-4-hydroxy-1,2,3-triazole-1-oxide of formula I (R = phenyl) is stirred in 1000 ml of glacial acetic acid, with ice cooling, with 75 g of zinc dust. After completion of the reaction, the filtrate is filtered off and concentrated by evaporation to dryness. The residue is stirred into water, filtered off under suction, washed with water and again filtered off under suction.

Yield: 70 g = 87% of theory.
M.P.: 124° C.

| Analysis: | C | H | N | O |
|---|---|---|---|---|
| calculated: | 59.6 | 4.35 | 26.1 | 9.95 |
| found: | 59.5 | 4.4 | 25.8 | 10.1. |

EXAMPLE 6

2-Phenyl-4-hydroxy-5-bromo-1,2,3-triazole 32.2 g of 2-phenyl-4-hydroxy-1,2,3-triazole is stirred in 400 ml of chloroform with 32 g of bromine at room temperature for 16 hours. The solvent is evaporated off and the residue is stirred into petroleum ether and filtered off under suction.

| Analysis: | C | H | Br | N |
|---|---|---|---|---|
| calculated: | 40.0 | 2.5 | 33.3 | 17.5 |
| found: | 40.8 | 2.6 | 35.0 | 17.4. |

EXAMPLE 7

40.25 g of 2-phenyl-4-hydroxy-1,2,3-triazole is placed into 500 ml of chloroform. 17.8 g of chlorine is then slowly introduced at room temperature, and stirring is maintained for 12 hours.

The reaction mixture is subsequently completely concentrated by evaporation, and the residue is stirred into petroleum ether and filtered off under suction.

Recrystallisation from ligroin yields 44 g of 2-phenyl-4-hydroxy-5-chloro-1,2,3-triazole (90% of theory), M.P. 135°–140° C.

| Analysis: | C | H | Cl | N |
|---|---|---|---|---|
| calculated: | 49.1 | 3.1 | 18.15 | 21.5 |
| found: | 50.1 | 3.3 | 17.1 | 22.0 |

Example 8

The following compounds of formula I are prepared analogously to Examples 1 – 4:

| R | M.P. |
|---|---|
| o-tolyl | 128–132° C |
| m-tolyl | 114–116° C |
| p-tolyl | 155–157° C |
| 3-chlorophenyl | 166–168° C |
| 4-chlorophenyl | 173–174° C |
| 2-methoxyphenyl | 149–152° C |
| 4-methoxyphenyl | 122–123° C |
| 2,5-dichlorophenyl | 153–155° C |
| 3,5-dichlorophenyl | 168° C |
| 4-bromophenyl | 175–177° C |
| 4-fluorophenyl | 182–184° C |
| 3-trifluoromethyl-phenyl | 139–142° C |
| 3-chloro-4-fluorophenyl | 170–172° C |
| 2-chloro-5-trifluoromethyl-phenyl | 164–167° C |

What we claim is:

1. Process for the preparation of 2-phenyl-4-hydroxy-1,2,3-triazole-1-oxides of formula I

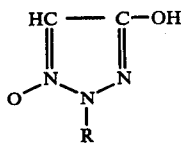

wherein R represents phenyl or phenyl substituted by halogen, alkyl, haloalkyl, cyano, alkoxy, nitro, alkoxycarbonyl, alkylthio, alkylsulphonyl, alkylsulphinyl, acetylamino, amino, monoalkylamino, dialkylamino, phenoxy or phenylsulfonyl groups, each of said alkyl substituents having 1–5 carbon atoms, wherein an oxime-hydrazone of formula II

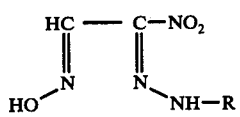

wherein R has the meaning given under formula I, is reacted in the presence of a $C_1$–$C_5$ alkane carboxylic acid at a temperature of between 15° and 100° C.

2. Process according to claim 1, wherein said carboxylic acid is acetic acid.

3. Process according to claim 1, wherein the reaction medium used is a mixture of said carboxylic acid and water, in which the water content is 5–25%.

4. Process according to claim 1, wherein the reaction temperature is between 20° and 30° C.

* * * * *